(12) United States Patent
Kato

(10) Patent No.: US 6,629,521 B1
(45) Date of Patent: Oct. 7, 2003

(54) OXYGEN SENSOR AND FEEDBACK SYSTEM FOR OUTBOARD MOTOR ENGINE

(75) Inventor: Masahiko Kato, Shizuoka (JP)

(73) Assignee: Yamaha Marine Kabushiki Kaisha, Shizuoka (JP)

( * ) Notice: Subject to any disclaimer, the term of this patent is extended or adjusted under 35 U.S.C. 154(b) by 0 days.

(21) Appl. No.: 09/583,006

(22) Filed: May 26, 2000

(30) Foreign Application Priority Data

May 26, 1999 (JP) ............................................ 11-147271

(51) Int. Cl.[7] ................................................ F02D 41/00
(52) U.S. Cl. ........................ 123/687; 123/689; 403/335; 285/405
(58) Field of Search ................................. 123/687, 689, 123/694, 695, 696, 679; 403/335, 336; 285/405; 415/229

(56) References Cited

U.S. PATENT DOCUMENTS 5,918,275 A   6/1999  Kato et al.
5,983,878 A  11/1999  Nonaka et al.
6,058,907 A   5/2000  Motose et al.

*Primary Examiner*—John Kwon
(74) *Attorney, Agent, or Firm*—Knobbe, Martens, Olson & Bear, LLP

(57) ABSTRACT

An outboard motor includes a sensor assembly having a housing with a sensor chamber, a sensor having a sensor element exposed to the sensor chamber, and a sleeve disposed in a passage extending from a combustion chamber of the outboard motor to the sensor chamber. The sleeve can have three flanges supporting the sleeve within the passage. Additionally, the sleeve can have an extension so as to allow the overall length of the sleeve to be varied in accordance with the desired resonance frequency of the sensor chamber. An engine of the outboard motor can also include a control system configured to control an air/fuel ratio of fuel charges delivered to a combustion chamber within the engine based on an output of the combustion condition sensor when the engine is in a first operational state and to control the air/fuel ratio, irrespective of the output of the combustion condition sensor, when the engine is in the second operational state.

35 Claims, 11 Drawing Sheets

OXYGEN SENSOR AND FEEDBACK SYSTEM FOR OUTBOARD MOTOR ENGINE

PRIORITY INFORMATION

This application is based on and claims priority to Japanese Patent Application No. 11-147271, filed May 26, 1999, the entire contents of which is hereby expressly incorporated reference.

BACKGROUND OF THE INVENTION

1. Field of the Invention

The present invention relates to an engine sensor and a feedback-control system for an engine. More specifically, the present invention relates to an improved engine sensor assembly used for a feedback-control system of an outboard motor engine.

2. Description of Related Art

In all fields of engine design, there is an increasing emphasis on obtaining more effective emission control, better fuel economy and, at the same time, continued high or higher power output. In pursuit of better fuel economy and emission control, various types of control systems have been developed in conjunction with internal combustion engines. One of the more effective types of controls is so-called "feedback" control. With this type of control, a basic air/fuel ratio is set for the engine. Adjustments are then made from the basic setting based upon the output of a sensor that senses the air/fuel ratio in the combustion chamber in order to bring the air/fuel ratio into the desired range.

Normally, the type of sensor employed for such feedback-control is an oxygen ($O_2$) sensor which outputs an electrical signal. Generally, when the output signal voltage is high, little oxygen is present in the exhaust, indicating that a combusted air/fuel charge was rich in fuel. On the other hand, when the output signal voltage is low, substantial amounts of oxygen are present in the exhaust, thus indicating that a combusted charge was rich in air.

A conventional oxygen sensor is normally associated with a wave forming circuit which manipulates the output of the sensor to indicate an "On" signal when the voltage of the output signal exceeds a reference voltage (i.e., a signal which results when the supplied charge is rich in fuel). On the other hand, the circuit manipulates the signal to indicate that the sensor is "off" when the voltage of the output signal does not exceed the reference voltage (i.e., a signal which results from a supplied charge is rich in air).

The control operates on a feedback-control principle, continuously making corrections to accommodate deviations from the desired air/fuel ratio. Adjustments are made in stepped intervals until the sensor output goes to the opposite sense from its previous signal. For example, if the mixture is too rich in fuel (i.e., the sensor signal is "on"), then lean adjustments are made until the mixture strength is sensed to be lean (i.e., the sensor signal turns "off"). Adjustments are then made back into the rich direction in order to approximately maintain the desired ratio.

Most commonly, the oxygen sensor is the type which utilizes inner and outer platinum or platinum coated electrodes. However, the platinum acts as a catalyst, which catalyzes exhaust. For example, oxygen remaining in the exhaust may be catalyzed with carbon monoxide at the platinum electrode interface, creating carbon dioxide. When the effects of the platinum in improving exhaust gas emissions may be advantageous, the oxygen content of the gas being sensed can be affected to a degree which causes the sensor to provide inaccurate data, causing the control to adjust the air/fuel ratio erroneously.

For example, while the actual oxygen content of the exhaust system may correspond to an air rich air/fuel charge such that the actual signal from the sensor should indicate that the sensor is "off" the above-described effect may cause the sensor to indicate little oxygen is present (i.e., as if a rich fuel charge has been supplied) by an "on" signal. In that instance, the feedback-control is arranged to adjust the air/fuel ratio in the fuel rich direction in response to the "on" signal even though the mixture is already fuel rich.

A known mounting arrangement for an oxygen sensor is illustrated in FIG. 1. As shown in FIG. 1, an oxygen sensor assembly 10 includes an oxygen sensor 12, an oxygen sensor housing 14, and a sleeve 16.

The housing assembly 14 includes a sensor chamber 18 defined in a housing body 20. A sensor element 22 of the oxygen sensor 12 is disposed within the sensor chamber 20. The sensor chamber 18 tapers radially inwardly towards a lower end thereof and communicates with a gas guide 24 via a communication passage 26. The housing body 20 is connected to an engine block 28 and communicates with a cylinder bore 30 defined in the cylinder block 28 via a throughole 32 which extends between the cylinder bore 30 and an outer surface of the engine body 28.

The sleeve 16 is disposed within the throughole 32. Additionally, the sleeve 16 includes an inner flange 34 disposed on an inner end of the sleeve, i.e., proximate to the cylinder bore 30 and an outer flange 36 disposed at a distal end of the sleeve 16, i.e., distal from the cylinder bore 30.

As shown in FIG. 1, the inner and outer flanges 34, 36 are relatively thick. Additionally, the inner flange 36 contacts both the engine body 28 and the housing body 20. Between the flanges 34, 36, and annular air gap 38 is formed between an outer surface of the sleeve 16 and an inner surface of the throughole 32.

SUMMARY OF THE INVENTION

One aspect of the present invention includes the realization that known engine sensing assemblies, such as oxygen sensor assemblies, have proven to be inadequate. In particular, it has been found that known combustion condition sensors do not satisfactorily maintain the temperature of combustion products for sensing purposes. For example, it has been found that sleeves, such as the sleeve 16 illustrated in FIG. 1, allow an excess amount of heat, under some operating conditions, to escape from the combustion gases flowing through the throughole 32, thus lowering the temperature of the gases sufficiently to prevent the reliable operation of the oxygen sensor. It has been found that the escaping heat is transferred into the housing body 20 of the sensor assembly 14 via one of the sleeve flanges.

As shown in FIG. 1, the inner flange 36 has a substantial thickness and contacts both the inner surface of the throughole 32 formed in the engine body 28 and the inner surface of the guide passage 24 formed in the housing body 20. Thus, heat from the combustion gases flowing through the sleeve 16 can be transferred into the housing body. 20 via the inner flange 36, thus cooling the sleeve 16. Additionally, heat can also be transferred between the engine body 28 and the housing body 20, because the flange 36 contacts both the engine body 28 and the housing body 20. It has been found that by constructing the sleeve 16 so as to have only two thick flanges 34, 36 at its proximate and distal ends, such that the outer flange 36 contacts both the throughole 32 formed in the engine body 28 and the guide passage 24 formed in the housing body 20, the sleeve 16 is excessively cooled, thereby allowing deposits to enter the guide passage 24 and damage the sensor element 22. Thus, it is desireable to provide a sleeve that better maintains the temperature of combustion gases flowing therethrough.

Heat stored in the sleeve 16 is also useful for burning deposits that may enter the sleeve 16, thus preventing such deposits from adhering to the sensor element 22 of the oxygen sensor 12. It has been found that by constructing the sleeve 16 so as to have only two thick flanges 34, 36 at its proximate and distal ends, such that the outer flange 36 overlaps both the throughole 32 formed in the engine body 28 and the guide passage 24 formed in the housing body 20, the sleeve 16 is excessively cooled, thereby allowing deposits to enter the guide passage 24 and damage the sensor element 22.

As noted above, direct injected engines are becoming more popular. In a direct injected engine, lubricant is delivered directly to the crankcase without being mixed with fuel. Thus, droplets of lubricant entering the combustion chamber are more viscous in direct injected engine as compared to engines which mix lubricant with fuel before injection. It has been found that such direct injected engines can suffer more frequent oxygen sensor failure due to the higher viscosity lubricant droplets that reach the oxygen sensor 12. Thus, it is advantageous to construct an engine sensor assembly such that the sleeve disposed in the throughole formed in the cylinder wall more reliably bums deposits, such as oily deposits, during operation of the engine, thereby preventing such deposits from reaching the engine sensor.

According to another aspect of the invention, a sensor assembly for an internal combustion engine comprises a sensor chamber, a sensor body having a sensor element disposed in the sensor chamber and a first passage connecting the combustion chamber of the engine with a sensor chamber. A sleeve extends through the first passage. The sleeve includes at least three flanges supporting the sleeve within the first passage so as to define a gap between an inner surface of the first passage and outer surface of the sleeve. By constructing the sleeve with at least three flanges, the thickness of each sleeve can be reduced as compared to the thickness required for sleeves having only two flanges. Thus, the heat transferred from the sleeve to the sensor housing can be reduced. Preferably, two of the three flanges are supported within a throughole defined in the engine body and only one flange is supported by the sensor housing. As noted above, by using three flanges, the flanges can be made thinner than the thickness required for sleeves having only two flanges. Additionally, by constructing the sleeve such that only one flange is supported by the sensor housing, there is less surface area contact between the sleeve and the sensor housing, thus further limiting transfer of heat from the sleeve to the sensor housing.

Another aspect of the invention includes the realization that thermal insulation provided by the sleeve is further enhanced if the inner diameter of the sleeve extending through the first passage is at least one-half as large as the outer diameter of the sleeve.

Thus, according to a further aspect of the invention, a sensor assembly for an internal combustion engine comprises a sensor chamber, a sensor body having a sensor element disposed in the sensor chamber, a first passage connecting the combustion chamber with a sensor chamber, and a sleeve extending at least partially through the first passage. An inner diameter of the sleeve is at least one-half as large as the outer diameter of the sleeve.

Another aspect of the invention includes the realization that the various passages and/or chambers which allow combustion gases to reach a combustion condition sensor of an internal combustion engine can be configured to define a resonance chamber. Depending on the relative sizes of the passages, chambers, and the corresponding combustion chamber, this resonance chamber can be tuned such that resonance frequency of the chamber is achieved at a frequency that corresponds to an engine speed that is within the normal range of operating speeds of the engine. However, it has been found that at resonance, a combustion condition sensor such as an oxygen sensor, can be damaged from overheating.

For example, at resonance, the relative movement between the combustion gases and the sleeve can increase significantly thereby increasing the rate of thermal conduction from the gases into the sleeve as well as the oxygen sensor. As the temperature of the sleeve rises, the temperature of the sensor chamber also rises, thus raising the temperature of the sensor itself and increasing the chance of damage to the sensor.

Thus, according to another aspect of the invention, a sensor assembly for an internal combustion engine includes a sensor and a housing defining a resonance chamber. The housing is configured to receive the sensor such that the sensor is exposed to the resonance chamber. In the present sensor assembly, the resonance chamber is configured such that a resonance frequency of the resonance chamber is not less than approximately the maximum rated speed of the engine. Thus, the sensor assembly is less likely to be subjected to significant resonance of the combustion gases during operation of the engine.

Yet another aspect of the invention includes the discovery that during certain states of engine operation, the output of certain combustion condition sensors does not reliably correspond to the actual combustion condition. For example, it has been found that when a throttle valve is opened greater than 50%, the flow of air into the combustion chamber, and thus a corresponding oxygen sensor communicating with the combustion chamber, is sufficiently large to cause the sensor to erroneously indicate that a lean mixture has been combusted. Such an erroneous lean mixture indication causes the engine controller to compensate by increasing the amount of fuel injected, thus wasting fuel. Similarly, at engine speeds above approximately 3000 rpm, the speed of induction air flowing into the cylinder and thus the sensor chamber, can also cause an oxygen sensor to erroneously indicate a lean mixture.

Accordingly, an internal combustion engine according to another aspect of the invention, comprises an engine body defining at least one combustion chamber and a charge former configured to deliver fuel charges to the engine body for combustion in the combustion chamber. A combustion condition sensor communicates with the combustion chamber. A controller controls the operation of the charge former in response to an output of the combustion condition sensor when the engine is in a first operational state. However, when the engine is in a second operation state, the controller controls the operation of the charge former irrespective of the output of the combustion condition sensor.

By including a controller which utilizes the combustion condition sensor output in one operational state for charge forming control but not during another operational state, the present internal combustion engine can more effectively prevent erroneous information from affecting the calculations performed for controlling the air/fuel ratio of the charge delivered to the engine body.

Further aspects, features and advantages of the present invention will become apparent from the detailed description of the preferred embodiments which follow.

Figure 2:
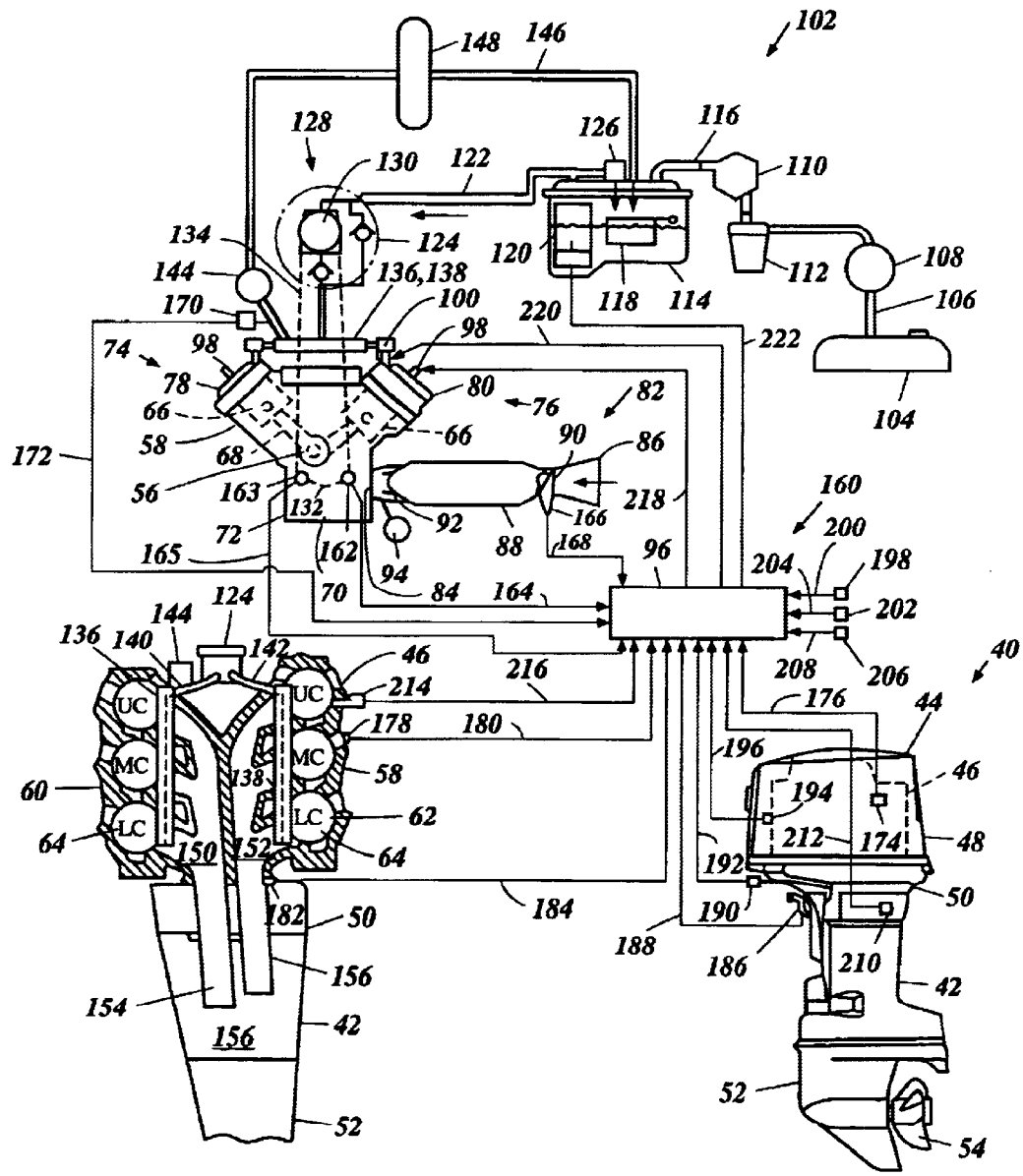

The features mentioned in the Summary of the Invention, as well as other features of the invention will now be described with reference to the drawings of several preferred embodiments of a sensor assembly and a controller for controlling an internal combustion engine. The illustrated embodiments are intended to illustrate, but not to limit the invention. The drawings contain the following figures:

FIG. 2 is a multipart view showing: in the lower right-hand portion, an outboard motor that employs a sensor assembly which relates to the present invention; in the upper view, a partially schematic top plan view of the engine of the outboard motor with its air induction and fuel injection system shown in part schematically; in the lower left-hand portion, a rear elevational view of the outboard motor with the portions removed and other portions broken away and shown in section so as to more clearly illustrate the construction of the engine; and the fuel injection system shown in part schematically. An ECU (electronic control unit) for the motor links the three views together.

Figure 3:
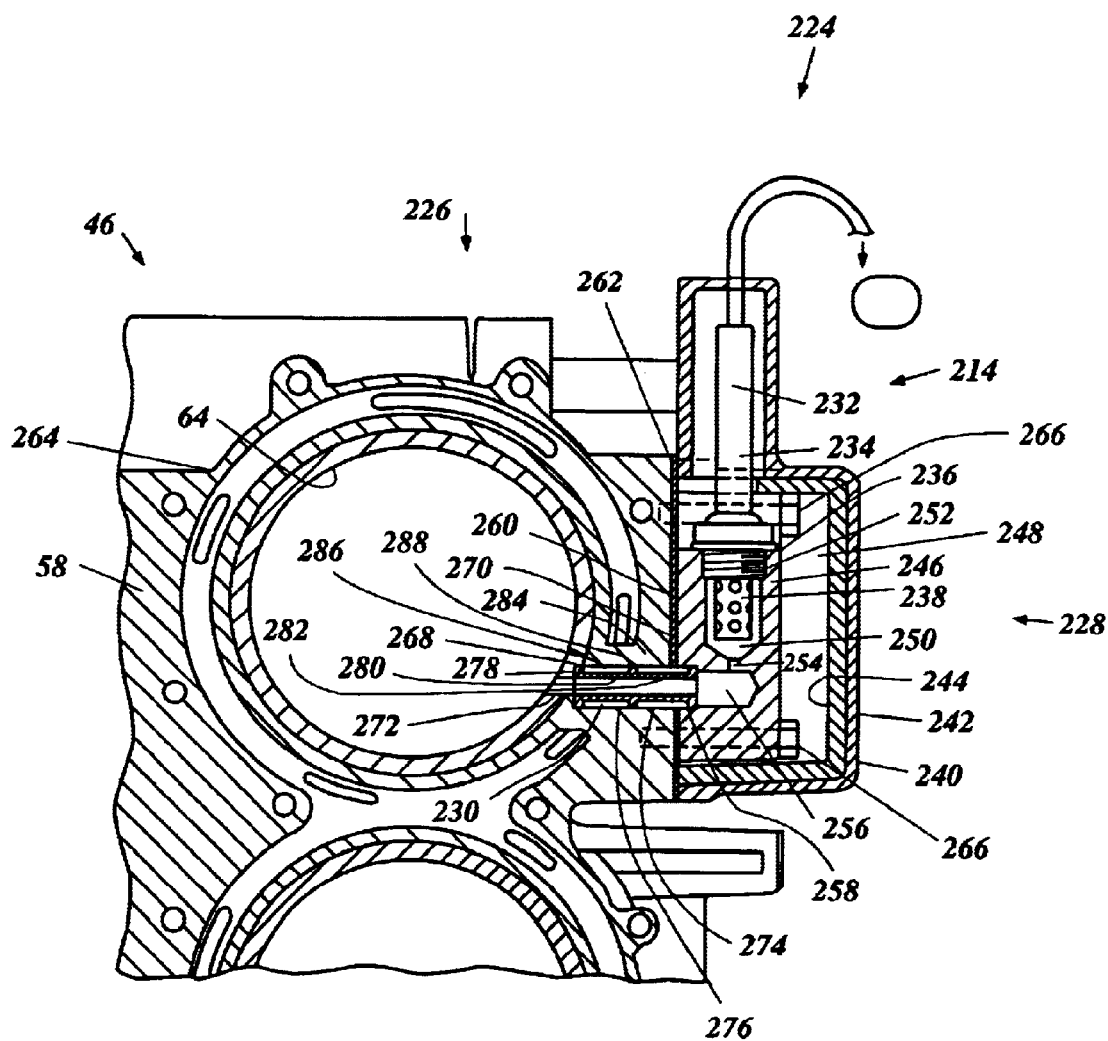

FIG. 3 is an enlarged cross-sectional view of the cylinder bore and sensor assembly shown in the upper right-hand portion of the engine illustrated in the lower left-hand portion of FIG. 2.

Figure 4:
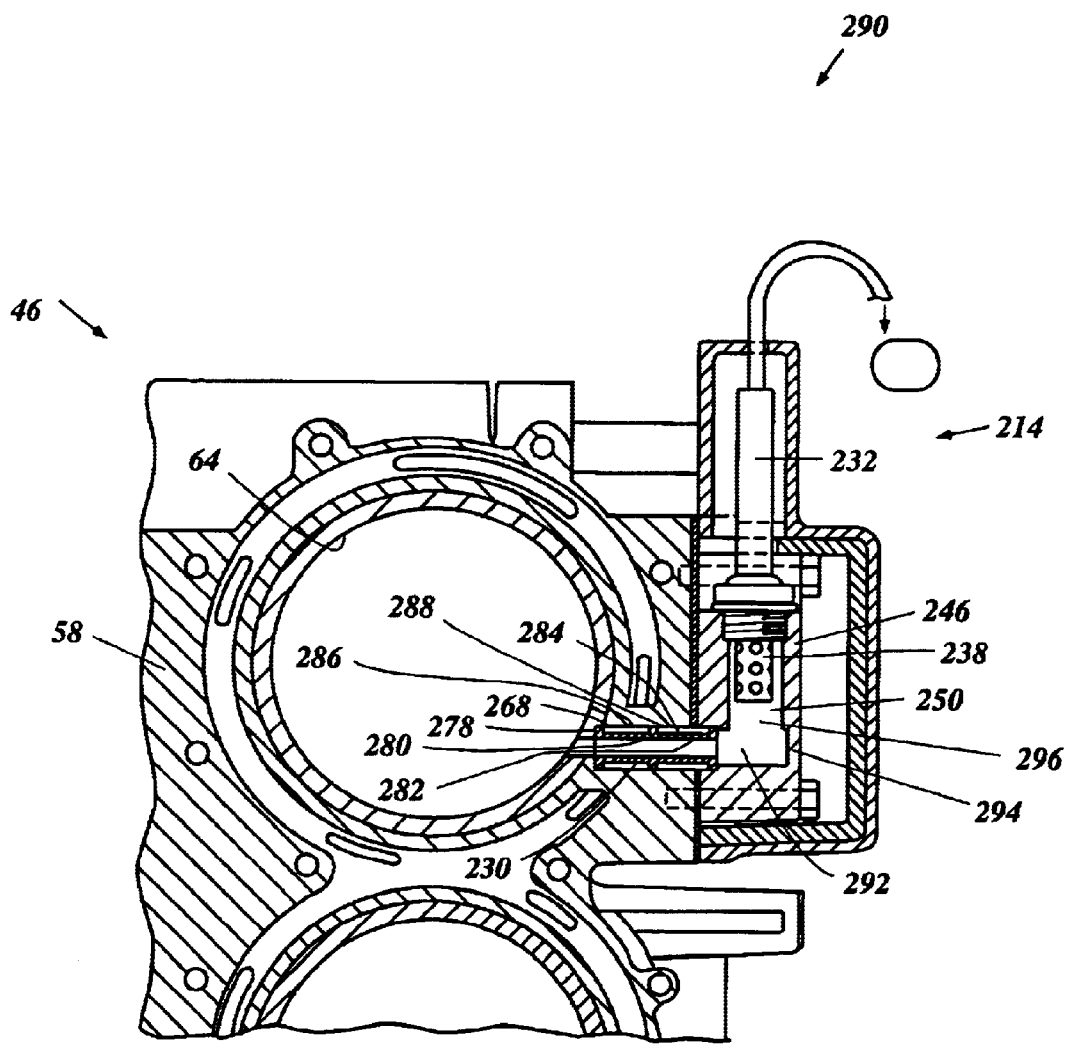

FIG. 4 is a modification of the sensor assembly illustrated in FIG. 3.

Figure 5:
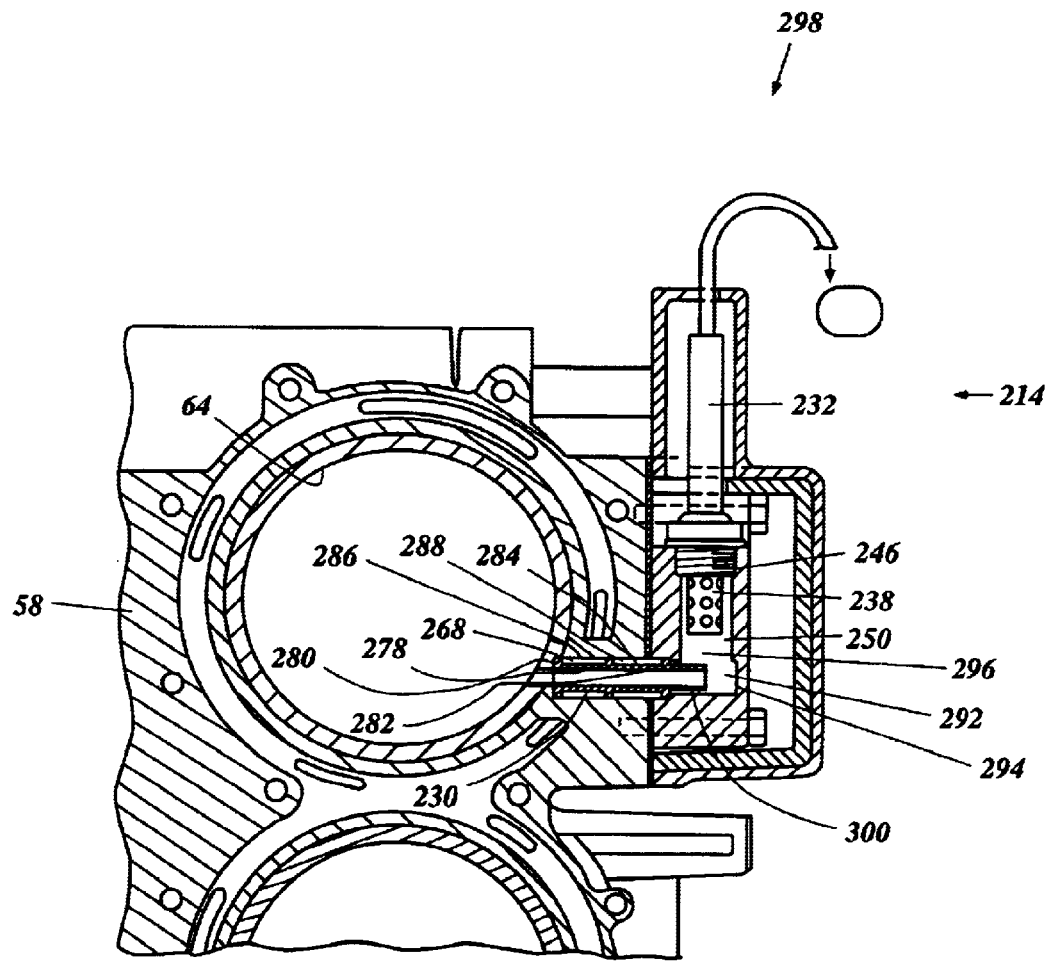

FIG. 5 is a further modification of the sensor assembly illustrated in FIG. 3.

Figure 6:
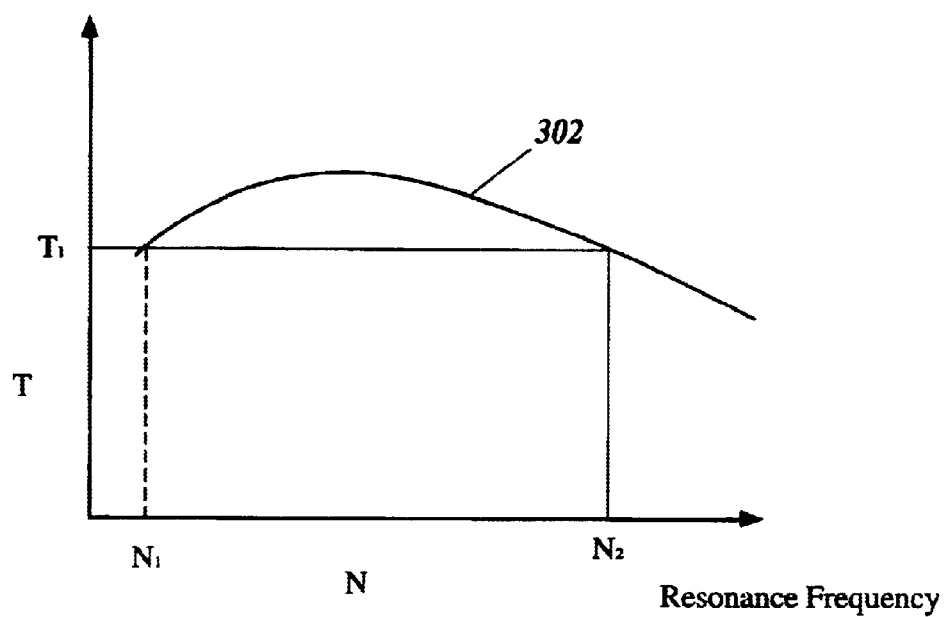

FIG. 6 is a graph illustrating a relationship between the temperature inside the assembly illustrated in FIGS. 3–5 as a function of resonance frequency.

Figure 7:
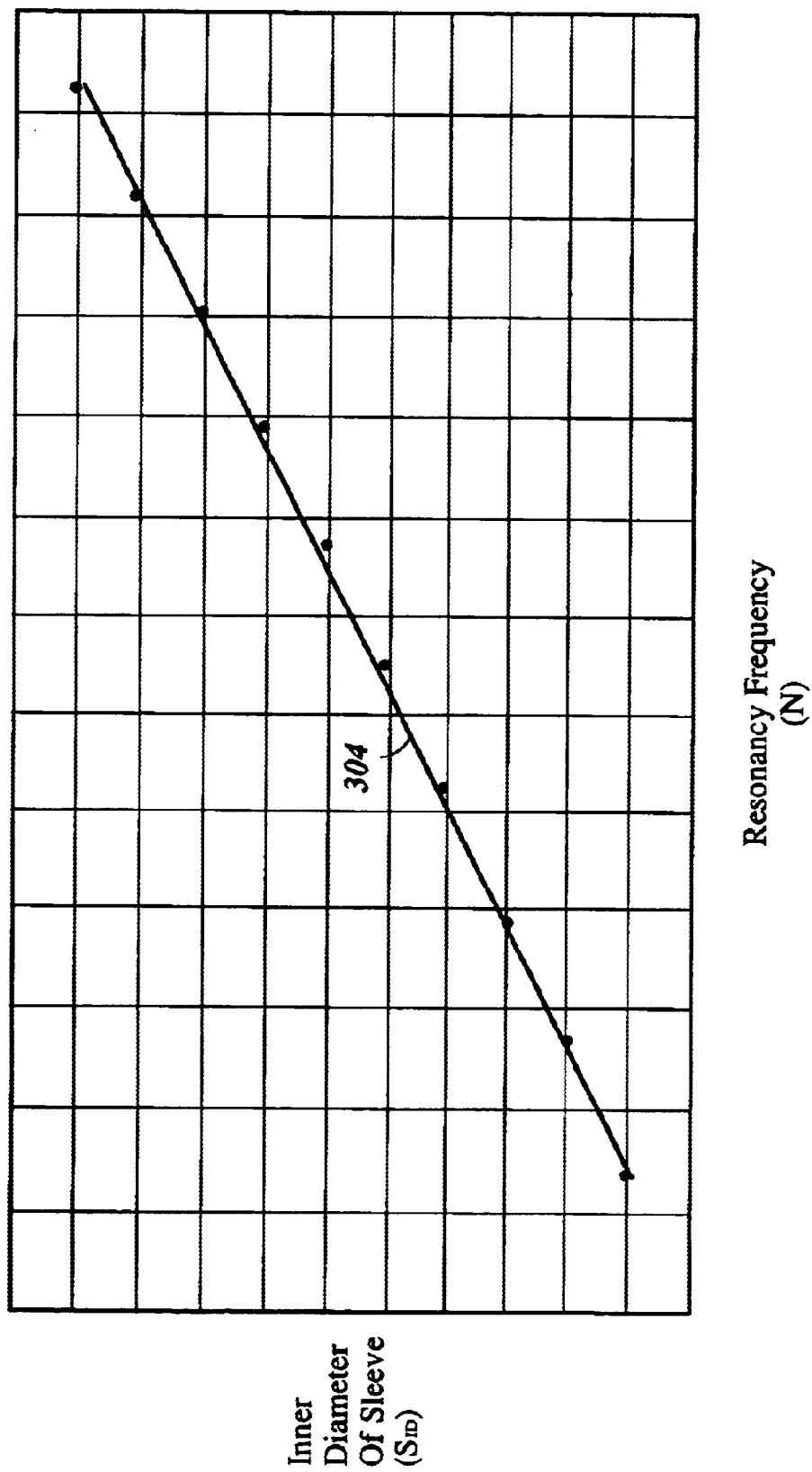

FIG. 7 is a graph illustrating a relationship between the inner diameter of the sleeve illustrated in FIGS. 3–5 plotted on the vertical axis as a function of resonance frequency plotted on the horizontal axis.

Figure 8:
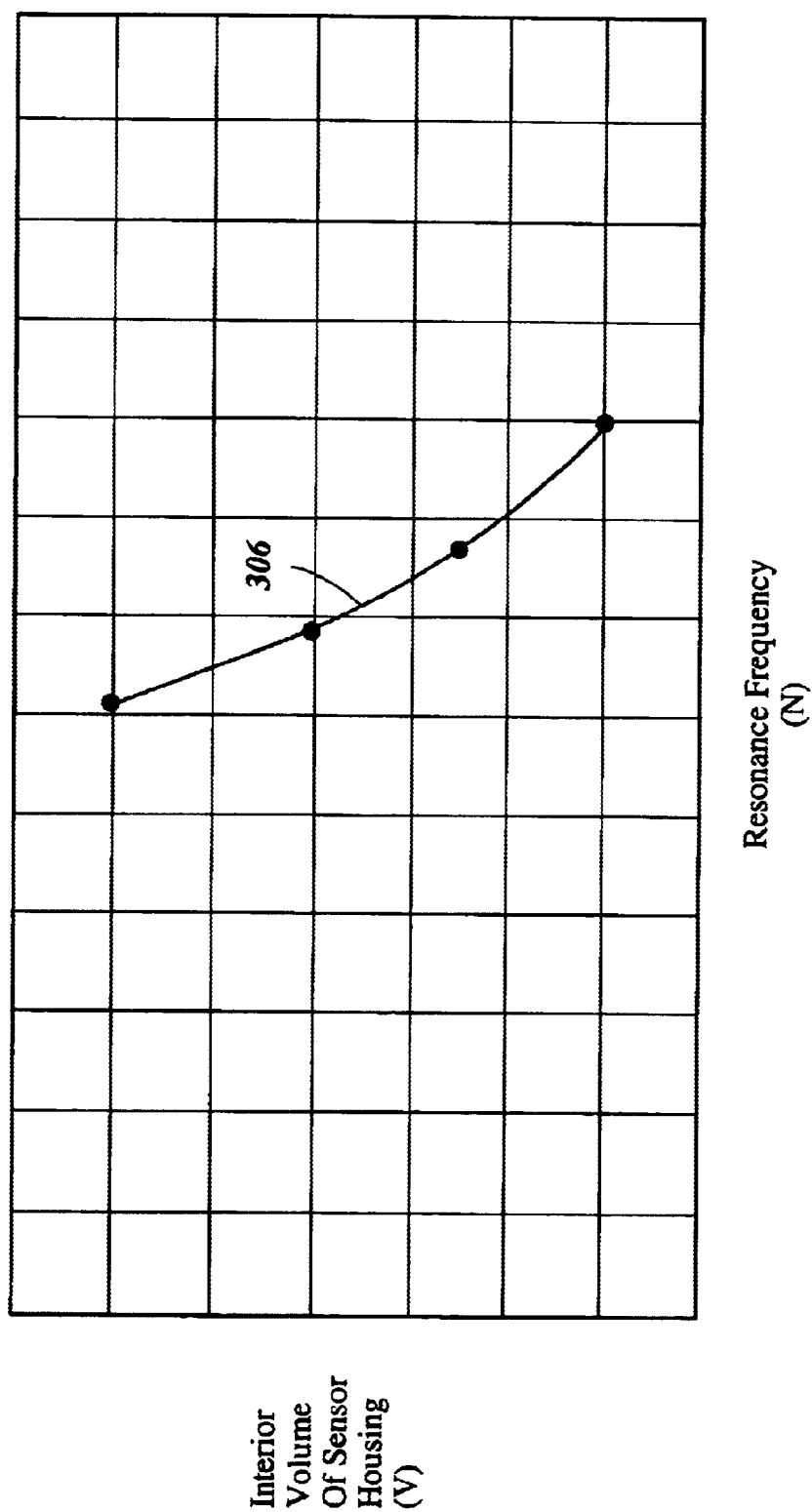

FIG. 8 is a graph illustrating a relationship between an internal volume of the assembly shown in FIGS. 3–5 plotted on the vertical axis and resonance frequency plotted on the horizontal axis.

Figure 9:
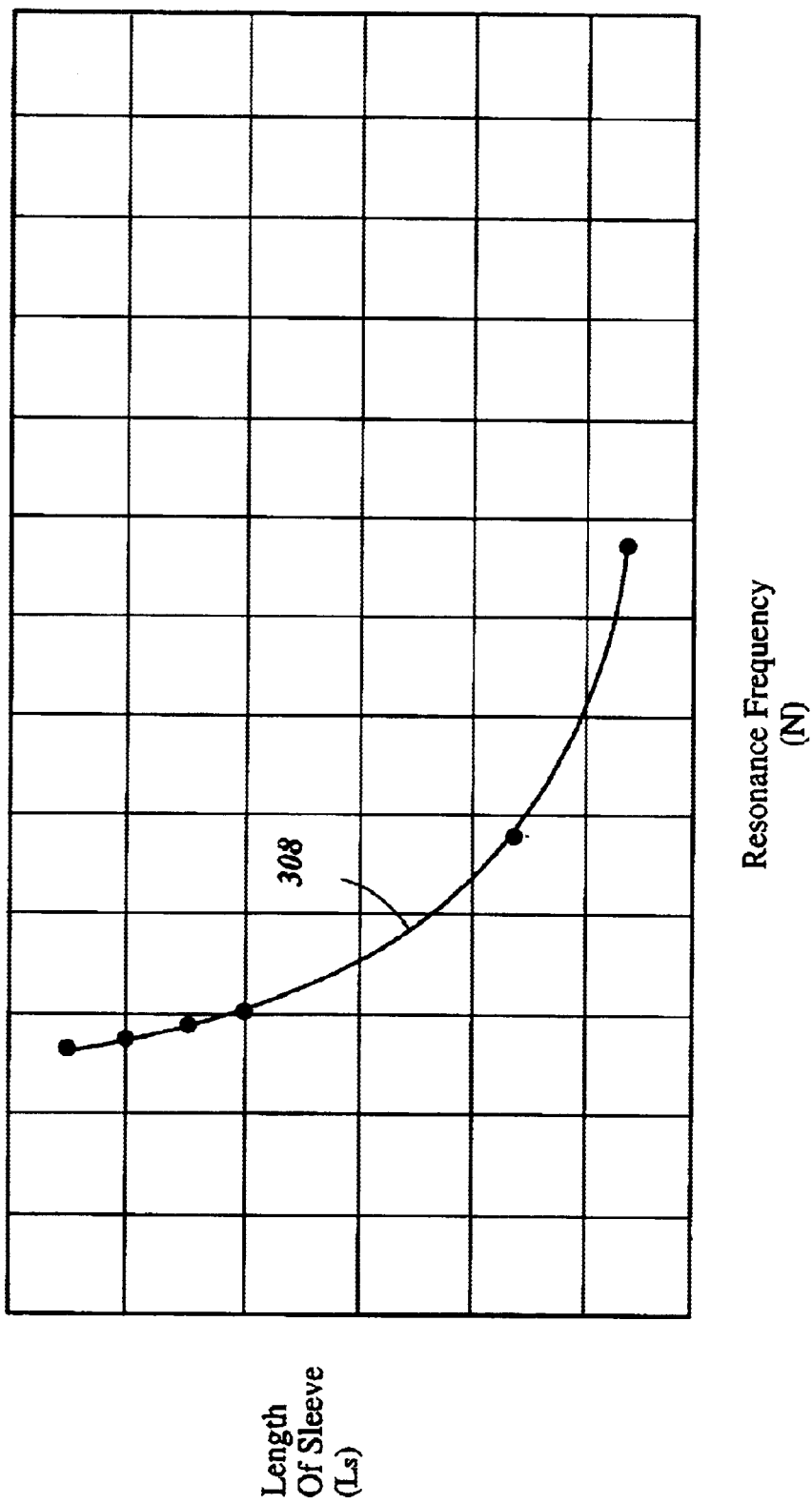

FIG. 9 is a graph illustrating a relationship between a length of a sleeve included in the assembly shown in FIGS. 3–5 and the resonance frequency plotted on the horizontal axis.

Figure 10:
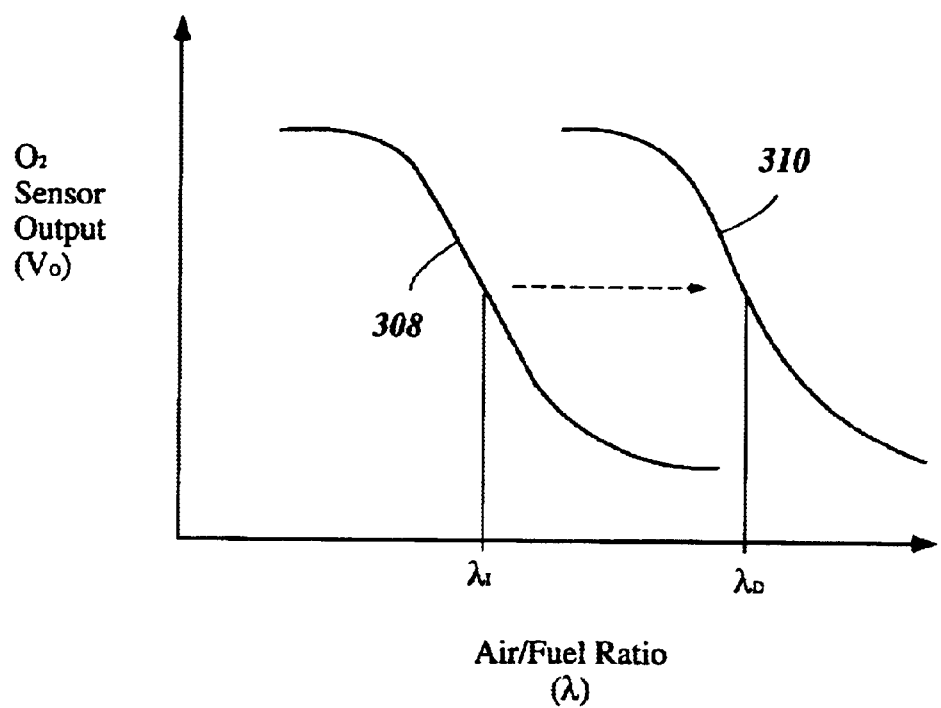

FIG. 10 is a graph illustrating a relationship between the output signal of an oxygen sensor plotted on the vertical axis as a function of the air/fuel ratio of two engines. One curve illustrates the relationship for an induction injection or carburated fuel system and the second curve illustrates the relationship for a direct injected engine.

Figure 11:
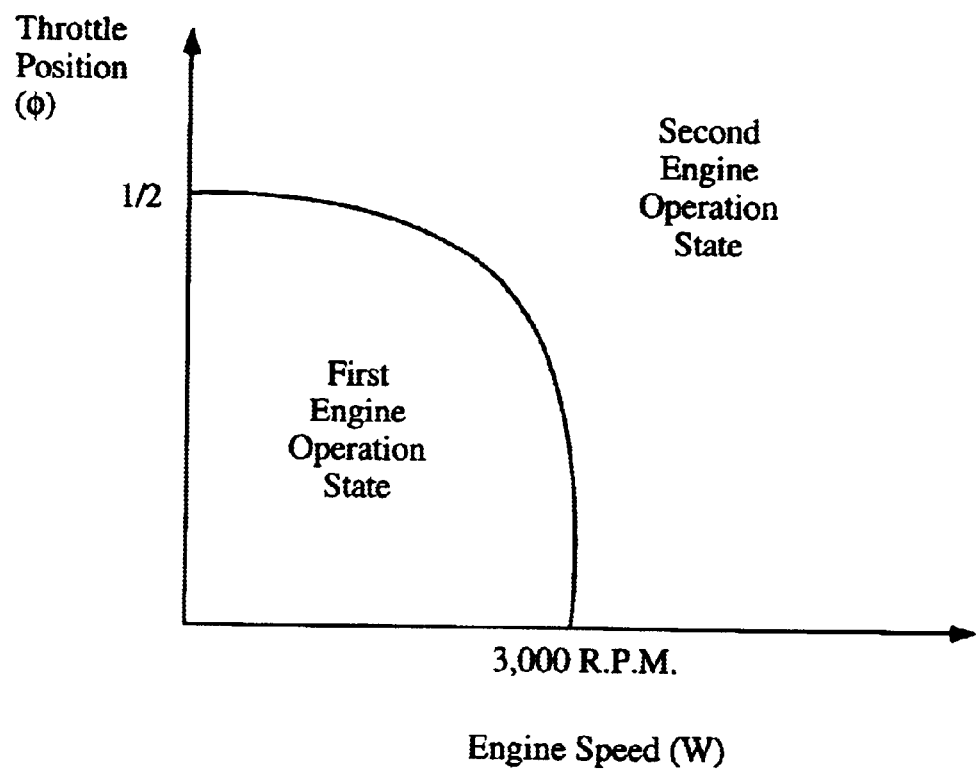

FIG. 11 is a graph illustrating throttle angle opening on the vertical axis and engine RPM on the horizontal axis. The curve plotted on the graph defines a boundary between a first engine operation state and a second engine operation state.

DETAILED DESCRIPTION OF THE PREFERRED EMBODIMENTS OF THE INVENTION

An improved sensor assembly for an outboard motor is disclosed herein. The assembly includes an improved structure for housing a combustion condition sensor for an internal combustion engine of an outboard motor, which provides better protection for the sensor. Thus, the risk of damage to the sensor is reduced which thereby increase the useful lifespan the sensor.

Figure 1:
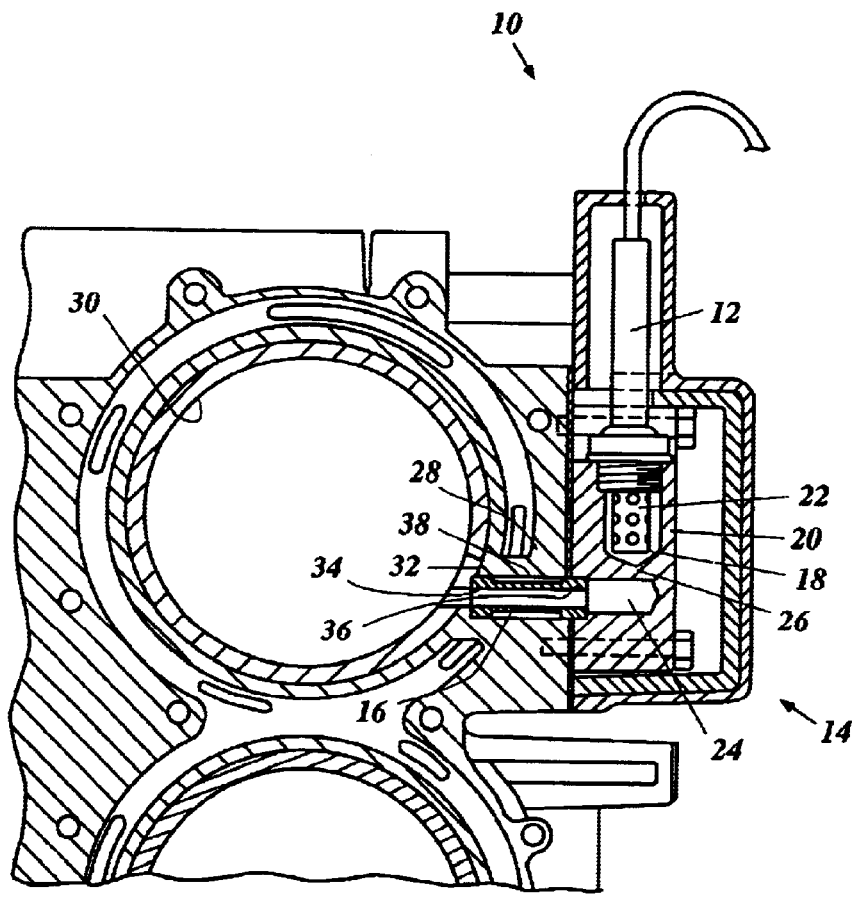
FIG. 1 is a cross-sectional side view of a portion of a known engine illustrating an oxygen sensor.

In the lower right-hand view of FIG. 1, an outboard motor is depicted in side elevational view and is identified generally by the reference numeral 40. The entire outboard motor 40 is not depicted in that the swivel bracket and clamping bracket that are typically associated with the driveshaft housing 42, are not illustrated. These components are well known in the art and the specific method by which the outboard motor 40 is mounted to the transom of an associated watercraft is not necessary to permit those skilled in the art to understand or practice the invention.

The outboard motor 40 includes a powerhead, indicated generally by the reference numeral 44, that is positioned above the driveshaft housing 42 and which includes an internal combustion engine, indicated generally by the reference numeral 46. The engine 46 is shown in more detail in the remaining two views of this figure and is described in more detail below.

The powerhead 44 is surrounded by a protective cowling that includes a main cowling member 48. The main cowling member 48 is detachably affixed to a lower tray portion 50 of the protective cowling. The lower tray portion 50 encloses an upper portion of the driveshaft housing 42.

Positioned beneath the driveshaft housing 42, a lower unit 52 is provided in which a propeller 54, which forms the propulsion device for the associated watercraft, is journaled.

As is typical with outboard motor practice, the engine 46 is supported in the powerhead 44 so that its crankshaft 56 (see upper view of FIG. 2) rotates about a vertically extending axis. This facilitates connection of the crankshaft 56 to a driveshaft (not shown) which depends into the driveshaft housing 42. The driveshaft drives the propeller 54 through a conventional forward, neutral, reverse transmission (not shown) contained in the lower unit 52.

The details of the construction of the outboard motor and the components which are not illustrated maybe considered to be conventional or of any type known. Those skilled in the art can readily refer to any known constructions with which to practice the invention.

With continued reference to FIG. 2, the engine 46 of the illustrated embodiment is a V6 type engine and operates on a two-stroke, crankcase compression principle. Although the invention is described in conjunction with an engine having a particular cylinder number and cylinder configuration, it will be readily apparent that the invention can be utilized with engines having other numbers of cylinders, other cylinder configurations (e.g., inline and W-type) and operating under other combustion principles (rotary, diesel, and four-stroke principles).

The engine 46 comprises a cylinder body or cylinder block 58 that forms a pair of cylinder banks 60, 62. Each cylinder bank 60, 62 is formed with three vertically spaced, horizontally extending cylinder bores 64 (cylinder sections are indicated as UC, MC, and LC).

Pistons 66 reciprocate in the cylinder bores 64. The pistons 66 are, in turn, connected to the upper or small ends of connecting rods 68. The big end of the connecting rods 68 are journaled on throws of the crankshaft 56 in a manner that is well known in the art.

The crankshaft 56 is journaled in a suitable manner for rotation within a crankcase chamber 70 that is formed in part by a crankcase member 72 affixed to the cylinder block 58 in a suitable manner. As is typical with two-cycle engines, the crankshaft 56 and the crankcase chamber 70 are formed with seals so that each section of the crankshaft that is associated with one of the cylinder bores 64 will be sealed from the others. This type of construction is well known in the art.

Cylinder head assemblies, indicated generally by the reference numerals 74, 76, are affixed to the end of the cylinder banks 60, 62, respectively, opposite the crankcase chamber 70. The cylinder head assemblies 74, 76 each include a plurality of recesses (not shown) on their inner faces. Each of these recesses cooperates with the cylinder bores 64 and the head of the pistons 66 to define combustion chambers of the engine 46. The cylinder head assemblies 74, 76 are preferably made of aluminum alloy die cast.

Cylinder head cover members 78, 80 cover the cylinder head assemblies 74, 76, respectively. The cylinder head cover members 78, 80 are affixed to the cylinder head members and to their respective cylinder banks 60, 62 in a suitable known manner. The cylinder head cover members 78, 80 preferably are also made of aluminum alloy die cast.

With reference to the upper portion of FIG. 2, an air induction system, indicated generally by the reference numeral 82, delivers an air charge to the sections of the crankcase chamber 70 associated with each of the cylinder bores 64. The communication is via an intake port 84 formed in the crankcase member 72 and registering with each of the crankcase chamber sections.

The induction system 82 includes an air silencing and inlet device, shown schematically in the figure and indicated by the reference numeral 86. The inlet device 86 supplies the induced air to a plurality of throttle bodies 88, each of which includes a throttle valve 90 provided therein. These throttle valves 90 are supported on throttle valve shafts (not shown). The throttle valve shafts are linked together for simultaneous opening and closing of the throttle valves 90 in a manner that is well known in the art.

The intake ports 84 include reed-type checkvalves 92. These checkvalves 92 permit the induced air to flow into the sections of the crankcase chamber 70 when the pistons 66 are moving upwardly in their respective cylinder bores 64. As the pistons 66 move downwardly, the charge will be compressed in the sections of the crankcase chamber 70. At that time, the reed-type checkvalves 92 will close to permit the charge to be compressed.

A lubricant pump 94 is provided for spraying lubricant into the throttle body 88 for engine lubrication under the control of an ECU (electronic control unit), shown schematically in FIG. 1 and identified by the reference numeral 96. Although it is not shown, some forms of direct lubrication may also be employed for delivering lubricant directly to other components of the engine.

The charge which is compressed in the sections of the crankcase chamber 70 is then transferred to the combustion chambers through a scavenging system. This scavenging system preferably is of the Schnurle type and includes a pair of main scavenge passages (not shown) that are positioned on diametrically opposite sides. These main scavenge passages terminate in main scavenge ports (not shown) so as to direct scavenge air flows into the combustion chamber of each cylinder bore 64. Additionally, auxiliary scavenge passages are preferably formed between the main scavenge passages and terminate in auxiliary scavenging ports which provide corresponding auxiliary scavenging air flows. Thus, during the scavenging stroke of the engine 46, the intake charge is transferred to the combustion chambers for further compression. As the pistons 66 move upwardly from their bottom end or bottom dead center position, the scavenge ports are closed and the charge is further compressed.

With reference to FIG. 2, sparkplugs 98 are affixed to the cylinder head assemblies 74, 76 and extend into the combustion chambers defined within the cylinder bores 64. In the illustrated embodiment, the sparkplugs 98 are disposed so as to extend along the axis of the corresponding cylinder bore 64. The sparkplugs 98 are fired under the control of the ECU 96. The ECU 96 receives certain signals, as will be described, for controlling the timing of firing of the sparkplugs 98 in accordance with any desired control strategy.

Each sparkplug 98, in turn, ignites a fuel-air charge that is formed from fuel sprayed by a fuel injector 100 into the air from the scavenge ports. In the illustrated embodiment, the fuel injectors 100 are solenoid-type and are electrically operated also under the control of the ECU 96. The fuel injectors 100 are mounted directly in the cylinder head assemblies 74, 76 in a specific location so as to provide optimum fuel vaporization under all running conditions.

Fuel is supplied to the fuel injectors 100 by a fuel supply system, indicated generally by the reference numeral 102 (see the upper view of FIG. 1). The fuel supply system 102 comprises a fuel tank 104 that is provided in a hull of watercraft with which the outboard motor 40 is associated. Fuel is drawn from the tank 104 through a conduit 106 via a first low pressure pump 108 and at least a second low pressure pump 110. The first low pressure pump 108 is manually operated pump and the second low pressure pump 110 is a diaphragm-type pump operated by variations in pressure in the various sections of the crankcase chamber 70, and thus generate a relatively low output pressure. A quick disconnect coupling (not shown) is provided in the conduit 106. Additionally, a fuel filter 112 is positioned in the conduit 106 at an appropriate location.

From the second low pressure pump 110, fuel is supplied to a vapor separator 114 which is mounted on the engine 46 or within the protective cowling 48 at an appropriate location. The fuel supplied through a fuel line 116. A float valve 118 (schematically represented in FIG. 2) is provided for maintaining a predetermined level of fuel within the vapor separator 114.

A high pressure electric fuel pump 120 is provided within the vapor separator 114, and pressurizes fuel from the vapor separator and directs the pressurized fuel into a fuel supply line 122. The fuel supply line 122 connects the high pressure electric fuel pump 120 with a high pressure fuel pump 124.

The electric fuel pump 120, which is driven by an electric motor, develops a pressure approximately between 3–10 kg/cm$^2$. A low pressure regulator 126 is connected to the fuel supply line 122 and limits the pressure that is delivered to the high pressure fuel pump 124 by dumping fuel back to the vapor separator 114 when the pressure in the fuel line 122 exceeds a predetermined pressure. The high pressure fuel pump 124 can develop a pressure of, for example, 50–100 kg/cm$^2$ or more. A pump drive unit 128 is provided for driving a high pressure fuel pump 124.

As shown in FIG. 2, the high pressure fuel pump 124 is mounted rearward from the engine block 58. The high pressure fuel pump 124 and the pump drive unit 128 are mounted to the cylinder block 58 in any appropriate manner. For example, the high pressure fuel pump 124 and the drive 128 can be mounted to the engine block 58 with a stay and a plurality of bolts (not shown).

The pump drive unit 128 comprises a pulley 130 affixed to a pump driveshaft (not shown) of the high pressure fuel pump 124, a drive pulley 132 affixed to the crankshaft 56 and a flexible transmitter 134. In the illustrated embodiment, the flexible transmitter 134 can be in the form of a smooth or toothed drivebelt. Accordingly, the pulleys 130, 132 can have smooth or toothed outer surfaces for cooperating with the flexible transmitter 134.

The pump driveshaft is provided with a cam disk (not shown) configured to operate plungers (not shown) disposed on the side of the high pressure fuel pump 124.

An outlet of the high pressure fuel pump 124 is connected to a pair of fuel rails 136, 138 via high pressure fuel lines 140, 142, respectively. The pressure of the fuel delivered to the fuel rails 136, 138 is regulated by a high pressure regulator 144 which is connected to an outlet of the high pressure fuel pump 124 or the fuel rails 136, 138. The high pressure regulator 144 returns fuel to the vapor separator 114 via a high pressure fuel return line 146. In the illustrated embodiment, a heat exchanger 148 is provided along the return line 146 so as to cool the fuel returning to the vapor separator 114. The pressure in the fuel rails 136, 138, thus is maintained at a substantially uniform level during operation.

The fuel rails 136, 138 preferably are formed of metal pipes so that the fuel rails are substantially rigid. The fuel rails 136, 138 are mounted to the cylinder head assemblies 74, 76, respectively and communicate with each of the fuel injectors 100. As noted above, during operation, fuel from the fuel injectors 100 mixes with air delivered to the cylinder bore 64 via scavenging ports. After the charge has been formed in the combustion chambers by the injection of fuel and air, the charge is fired by the sparkplugs 98. The injection timing and duration, as well as the control of timing of firing of the sparkplugs 98, are controlled by the ECU 96.

Once the charge burns and expands, the pistons 58 are driven downwardly in the cylinder bore 64 until the pistons 58 reach the lowermost position. As the pistons 58 move downwardly, an exhaust port (not shown) is uncovered so as to open the cylinder bore 64 with exhaust passages formed in the cylinder block 58. The exhaust gases flow through the exhaust passages to manifold collector sections 150, 152 of respective exhaust manifolds that are formed within the cylinder block 58.

A pair of exhaust pipes 154, 156 depend from an exhaust guideplate formed in the lower tray portion 50 and extend into an expansion chamber 158 formed in the driveshaft housing 42. From the expansion chamber 158, the exhaust gases are discharged to atmosphere through a suitable exhaust system.

Preferably, the exhaust system can include an underwater, high speed exhaust gas discharge and an abovewater, low speed exhaust gas discharge. Since these types of systems are well known in the art, a further description of the exhaust system is not believed to be necessary to permit those skilled in the art to practice the invention.

A feedback-control system, indicated generally by the reference numeral 160, controls the timing and duration of fuel injection from the fuel injectors 100 and the timing of the firing of the sparkplug 98. The feedback-control system 160 comprises the ECU 96 and a number of sensors configured to output a signal indicative of various conditions including, for example but without limitation, engine running conditions, ambient conditions or conditions of the outboard motor 40 that affect engine performance.

Certain sensors are schematically represented in FIG. 2. For example, an engine speed sensor 162 is mounted in vicinity of the crankshaft 56 and/or a flywheel attached to the crankshaft 56. The engine speed sensor 162 outputs a signal indicative of the position of the crankshaft 56 and/or the speed of rotation of the crankshaft 56. The signal from the engine speed sensor 162 is transferred to the ECU 96 via a crankshaft position data line 164.

A crankshaft position sensor 163 can also be mounted in the vicinity of the crankshaft so as to detect a position of the crankshaft. The output signal from the crankshaft position sensor 163 is transferred to the ECU 96 via a crankshaft position data line 165. As such, the ECU can receive the output signal from the crankshaft position sensor 163 for use in determining proper fuel injection timing and spark plug firing, for example.

A throttle position sensor 166 can be mounted in the vicinity of the throttle valve 90. The throttle valve position sensor 166 outputs a signal indicative of the throttle position of the throttle valve 90 so as to detect a position of the throttle valve 90. The signal from the throttle valve position sensor 166 is transferred to the ECU 96 via a throttle position data line 168. As such, the output of the throttle position sensor 166 can be used by the ECU 96 as an indication of operator demand or engine load.

For example, when an operator of the outboard motor 40 desires to accelerate an associated watercraft, the operator advances a throttle actuator (not shown) and further opens the throttle valve 90, thus increasing the load on the engine.

A pressure sensor 170 can be connected to the high pressure fuel return line 146 so as to detect a fuel pressure in the return line 146. The pressure sensor 170 is connected to the ECU 96 via a high pressure fuel return line data line 172. Thus, the ECU 96 can receive a signal from the high pressure fuel line sensor 170 which is indicative of the pressure in the high pressure fuel line 146.

A coolant temperature sensor 174 (see the lower right-hand side of FIG. 2) can be connected to a coolant jacket (not shown) provided on the engine 46 so as to detect a temperature of coolant flowing in the coolant jacket. The coolant temperature sensor 174 is connected to the ECU 96 via a coolant temperature data line 176. As such, the ECU 96 can receive a signal from the coolant temperature sensor 174 indicative of the temperature of coolant flowing through the cooling jacket provided in the engine 46.

An engine temperature sensor 178 can also be connected to the engine block 58. The engine temperature sensor 178 is connected to the ECU 96 via an engine temperature data line 180. As such, the ECU 96 can receive a signal from the engine temperature sensor 178 indicative of the temperature of the engine block 58.

A back pressure sensor 182 can be connected to the exhaust system of the engine 46. For example, in the illustrated embodiment, the back pressure sensor 182 is connected to an exhaust collection passage 152. The back pressure sensor 182 is connected to the ECU 96 via a back pressure data line 184. As such, the ECU 96 can receive a signal from the back pressure sensor 182 indicative of a back pressure in the exhaust passage 152.

A trim angle sensor 186 can be connected to the outboard motor 40 so as to sense a trim angle of the outboard motor 40. The trim angle sensor is connected to the ECU 96 via a trim angle data line 188. As such, the ECU 96 can receive a signal from the trim angle sensor 186 that is indicative a trim angle of the outboard motor 40.

A mount height sensor 190 can be connected to the outboard motor 40 so as to detect a height of the outboard motor 40. The height sensor 190 is connected to the ECU 96 via an engine height data line 192. As such, the ECU 96 can receive a signal from the sensor 190 that is indicative of the engine height.

An engine vibration sensor 194 can be mounted to the engine 46 so as to sense a vibration of the engine 46. The engine vibration sensor 194 is connected to the ECU 96 via an engine vibration data line 196. As such, the ECU 96 can receive a signal from the engine vibration sensor 194 that is indicative of the vibration of the engine 46.

A watercraft speed sensor 198 can be connected to a watercraft associated with the outboard motor 40 for detecting a speed of the watercraft. The watercraft speed sensor 198 is connected to the ECU 96 via a watercraft speed data line 200. As such, the ECU 96 can receive a signal from the watercraft speed sensor 198 that is indicative of a speed of the associated watercraft.

A watercraft position sensor 202 can be mounted to the associated watercraft for sensing the orientation of the watercraft including pitch and/or roll orientations of the watercraft. The watercraft position sensor 220 is connected to the ECU 96 via a watercraft position data line 204. As such, the ECU 96 can receive a signal from the watercraft position sensor which is indicative of the position of the watercraft.

An atmospheric pressure sensor 206 can be connected to the associated watercraft or any appropriate position on the outboard motor 40 for sensing a pressure of the atmosphere surrounding the outboard motor 40. The atmospheric pressure sensor 206 is connected to the ECU 96 via an atmospheric pressure data line 208. As such, the ECU 96 can receive a signal from the atmospheric pressure sensor 206 that is indicative of the atmospheric pressure surrounding the outboard motor 40.

A neutral sensor 210 can be connected to the outboard motor 40 for sensing when the forward reverse neutral transmission is in the neutral position. The neural position sensor 210 is connected to the ECU 96 via a neutral position sensor data line 212. As such, the ECU 96 can receive a signal from the neutral position sensor 210 that is indicative of whether the transmission is in the neutral position.

A combustion condition sensor 214 can be connected to any appropriate position on the engine 46 for detecting a combustion condition of the engine 46. The combustion condition sensor 216 is connected to the ECU 96 via a combustion condition data line 216. As such, the ECU 96 can receive a signal from the combustion condition sensor 214 that is indicative of a combustion condition occurring during the operation of the engine 46. The details of a mounting assembly for mounting the combustion condition sensor 214 is described below in further detail with reference to FIGS. 3–5.

In addition to the sensors described above, additional sensors may be provided for detecting other conditions such as an induction system air pressure sensor, an induction system air temperature sensor, a knock sensor, and various other sensors for use in accordance with various control strategies.

The ECU 96, as noted above, outputs signals to the fuel injectors 100, the sparkplugs 98, and the high pressure electric fuel pump 120 for their respective control. In the illustrated embodiment, the ECU 96 outputs a signal to the sparkplugs 98 via a sparkplug control data line 218. The ECU 96 outputs a control signal to the fuel injectors 100 via a fuel injector control line 220. The ECU 96 outputs a control signal to the high pressure electric fuel pump 120 via a fuel pump control line 220. Additionally, the ECU 96 can be connected to various other components of the engine 46 including, for example, but without limitation, a lubrication pump, and a coolant fluid pump. As noted above, the ECU 96 can control these various components according to any known control strategy.

With reference to FIG. 3, a combustion condition sensor mounting assembly 224 is illustrated as being mounted to an engine body 226 of the engine 46. In the illustrated embodiment, the mounting assembly 224 is connected to cylinder block 58.

As shown in FIG. 3, the combustion condition sensor mounting assembly 224 comprises the combustion condition sensor 214, a housing 228 and a sleeve 230.

In the illustrated embodiment, the combustion condition sensor 214 is an oxygen sensor 232. The oxygen sensor 232 comprises a sensor body 234 having an engaging portion 236 and a sensor element 238. Preferably, the oxygen sensor 232 is in the form of a catalytic type oxygen sensor. For example, the sensor element 238 of the oxygen sensor 232 can be formed of a ceramic material such as zirconium dioxide ($ZrO_2$) housed in a gas permeable platinum electrode. During operation, and in particular at temperatures in excess of 300° C., the zirconium dioxide conducts negative oxygen ions. Such a sensor is designed to be very responsive at Lambda ($\Lambda$) values in the vicinity of one (1), i.e., the output signal changes quickly in response to small changes in the detected air/fuel ratio. For typical gasoline powered engines, the stochiometrically ideal air/fuel ratio is about 14.7:1. As is common in the art, Lambda ($\Lambda$) is defined as equal to one (1) when the air/fuel ratio is 14.7:1. Thus, typical oxygen sensors for gasoline powered internal combustion engines are configured to be very responsive when the air/fuel ratio is about 14.7:1, i.e., at Lambda ($\Lambda$) values in the vicinity of one. The preferred operating temper range for such oxygen sensors is about 300° C. to 600° C. Typical oxygen sensors can be damaged if exposed to temperatures above 850° C.

A first electrode of the sensor is typically exposed to a reference value of atmospheric air. Thus, a greater quantity of oxygen ions will be present on the first electrode. Through the electrolytic action, the oxygen ions permeate the electrode and migrate through the electrolyte zirconium dioxide. Thus, a charge builds in the sensor as a function of the amount of oxygen ions that are present in the vicinity of the sensor element 238.

When the sensor element 238, i.e., the second electrode, is exposed to exhaust emissions formed as a result of the combustion of a rich air fuel mixture, there is very little free oxygen in the exhaust gas. This small amount of oxygen is readily combined with carbon monoxide (CO) present in the exhaust through the catalytic action of the platinum electrode. Thus, the oxygen concentration in the exhaust gases discharge after combustion of a rich air fuel charge is relatively low, in contrast with the oxygen content of the atmosphere. Oxygen atoms contacting the atmospheric electrode gain electrons and travel through the zirconius ceramic to the exhaust electrode where they then shed the extra electron, thus leaving a positive charge on the atmospheric electrode and a negative charge on the exhaust electrode. Through this mechanism a small voltage of about 0.8 volts can be generated by the sensor.

Conversely, when the outer platinum electrode is subjected to the emissions of the combustion of a lean air fuel charge, the concentration of free oxygen in the exhaust gas is relatively large. Thus, despite the oxidizing action of the platinum electrode, there is a relatively large amount of oxygen present in the exhaust gases exposed to the sensor element 238. Because there are oxygen ions present at both the exhaust electrode, i.e., the sensor element 238, and the atmospheric electrode (not shown), little electromotive force is generated between the electrodes, thereby leaving a charge of approximately 0 volts in the sensor. Alternatively, other types of oxygen sensors can be used.

As shown in FIG. 3, the oxygen sensor 232 is mounted within a housing 228. The housing 228 comprises an outer housing member 240 which is preferably formed of sheet metal. An insulating shell 242 is provided within the outer housing member 240. The insulation shell 242 is preferably formed from a suitable insulating material having a low coefficient of thermal conductivity and which has an inner surface 244 that is spaced from an inner housing member 246 so as to provide an insulating air gap 248.

The inner housing member 246 includes a sensor chamber 250 which is sized to receive the sensor element 238 of the combustion condition sensor 214. At an upper end of the sensor chamber 250, the inner housing member 246 includes an engaging portion 252 which is configured to releasably engage the engaging portion 236 of the combustion condition sensor 214. In the illustrated embodiment, the corresponding engaging portions 236, 252 include machine threads. Additionally, the combustion condition sensor 214 and the inner housing member 246 are configured so as to provide a seal between the combustion condition sensor 214 and an upper surface of the inner housing member 246.

As shown in FIG. 3, at a lower end of the sensor chamber 250, the inner housing member 246 includes a communication passage 254 that extends downwardly from the sensor chamber 250 and to a guide passage 256.

As viewed in FIG. 3, the guide passage 256 extends generally horizontally towards the cylinder bore 64 of the engine block 58. Additionally, the guide passage includes an enlarged end 258 which opens to an inner surface 260 of the inner member 246. A heat insulating gasket 262 is disposed between the inner housing member 246 and the engine block 58 so as to attenuate heat transfer between the sensor chamber 250 and the engine body. As has been noted, the engine 46 is a water cooled engine and the cooling jackets which surround the cylinder bore 64 are indicated generally by the reference numeral 264. The inner housing member 246 is connected to the cylinder block 58 via a plurality of bolts 266. The insulating shell 242 and the outer housing member 240 are installed over the inner housing member 246 and the bolts 266, and are attached to the cylinder block 58 with any appropriate fasteners.

As noted above, with reference to FIG. 2, the engine 46 is oriented such that the cylinder bore 64 extends generally horizontally, as is common in outboard motor practice. As shown in FIG. 3, the assembly 224 is oriented such that the combustion condition sensor 214 extends generally vertically. As such, water that may inadvertently reach the guide passage 256 is less likely to contact the sensor element 238.

As shown in FIG. 3, the guide passage 256 is positioned so as to communicate with a throughole 268. As shown in FIG. 3, the throughole 268 extends from the cylinder bore 64 to an outer surface 270 of the cylinder block 58. Additionally, the throughole 268 includes a narrowed portion 272 at the end of the throughole 268 proximate to the cylinder bore 64 and an enlarged portion 274 at the end of the throughole 268 distal from the cylinder bore 64 and which is open at the outer surface 270 of the cylinder block 58.

The sleeve 230 is disposed within the enlarged portion 274 of the throughole 268 and extends at least partially into the enlarged portion 258 of the guide passage 256. In the illustrated embodiment, the sleeve 230 comprises a tubular body 276 and three flanges; an inner flange 278, a middle flange 280 and an outer flange 282. As shown in FIG. 3, the inner flange 278 is provided at an inner end of the sleeve 230, i.e., the end of the sleeve 230 that is proximate to the cylinder bore 64. The outer flange 282 is provided at the outer end of the sleeve 230, i.e., the end of the sleeve 230 that is distal from the cylinder bore 64. Additionally, the middle flange 280 is provided between the flanges 278, 282.

As shown in FIG. 3, the flanges 278, 280, 281, extend from an outer surface 284 of the sleeve 230. Thus, when positioned in the enlarged portion 274 of the throughole 268, the flanges 278, 280, 282 define annular spaces 286, 288 between the outer surface 284 and the inner surface of the throughhole 268. Thus, the portions of the outer surface 284 of the sleeve 230 disposed between the inner flange 282 and the middle flange 280 and between the middle flange 280 and the outer flange 278 define reduced diameter portions of the outer surface 284. These reduced diameter portions of the outer surface 284 cooperate with the flanges 278, 280, 282 and the inner surface of the throughole 268 to define the annular insulating spaces 286, 288. The insulating spaces 286, 288 thus attenuate the transfer of heat through the sleeve 230 to the cylinder block 58 and to the inner housing member 246.

In operation, as a fuel air charges combusted within the cylinder bore 64, the exhaust gases travel through the throughole 268, the sleeve 230, the guide passage 256, the communication passage 254, and into the sensor chamber 250. After the exhaust gases have reached the sensor chamber 250, the exhaust gases interact with the sensor element 238 and cause the output signal of the oxygen sensor 232 to vary in accordance with the amount of oxygen present in the exhaust gases, as noted above.

As shown in FIG. 3, the inner and middle flanges 278, 280 contact the inner surface of the enlarged portion 274 defined within the cylinder block 58. Thus, only one flange, i.e., the outer flange 282, contacts the inner housing member 246. Thus, heat can only be directly conducted from the sleeve 230 via the outer flange 282. Additionally, by providing the sleeve 230 with three flanges 278, 280, 282, the outer flange 282 can be made thinner as compared to a sleeve that has only two flanges, such as the sleeve 16 illustrated in FIG. 1. Thus, the strength imparted to the sleeve 230 by the inclusion of an additional flange e.g., the middle flange 280, allows the outer flange 282 to be made thinner than the flanges of known sleeves, thus, reducing the rate of heat transfer from the sleeve 230 to the inner housing member 246.

As noted above, the temperature operating range of oxygen sensors is typically between 300° C.–600° C. Thus, by reducing the contact between the sleeve 230 and the inner housing member 246, the sleeve 230 can maintain a higher temperature as compared to sleeves of the prior art, such as the sleeve 16 illustrated in FIG. 1.

This is particularly advantageous for direct injected engines. For example, direct injected engines, such as the engine 46, inject fuel directly into the cylinder bore 64. Thus, lubricant which is provided to the crankcase chamber 70, is not diluted with fuel, unlike engines which incorporate induction injection or carbueration. Thus, lubricant droplets which have not been diluted or thinned with fuel, can enter the combustion chamber and pass into the throughole 268. When such a droplet of undiluted or unthinned lubricant enters the throughole 268, it is advantageous for the droplet to be combusted by contact with hot gases and/or an inner surface of the sleeve 230. However, because the droplet is not thinned or diluted with fuel, it is more viscous and thus more difficult to combust. Therefore, by constructing the sleeve 230 so as to maintain a higher temperature than sleeves of the prior art, the sleeve 230 is better able to combust undiluted droplets of lubricant that may enter the throughole 268, and prevent such droplets from reaching and therefore damaging the sensor element 238 of the oxygen sensor 232.

FIG. 4 illustrates a modification of the combustion condition sensor assembly 224 illustrated in FIG. 3. As shown in FIG. 4, a combustion condition sensor assembly 290 is constructed substantially identical to the assembly 224 illustrated in FIG. 3, except as noted below.

As shown in FIG. 4, the combustion condition sensor assembly 290 includes an oxygen sensor 232 having a sensor element 238 received within a sensor chamber 250. In the present modification, the guide passage 292 is larger than the guide passage 256 illustrated in FIG. 3. In particular, an inner end 294 of the guide passage 292 has been extended into the inner member 246 to a depth deeper than the guide passage 256. Additionally, the inner end 294 is formed to have a blunt shape, as compared to the inner end of the guide passage 256 illustrated in FIG. 3. Additionally, a communication passage 296 connecting the sensor chamber 250 with the guide passage 292 is provided with an inner diameter that is larger than the outer diameter of the sensor element 238. In the illustrated embodiment, the inner diameter of the communication passage 296 is substantially the same as the inner diameter of the sensor chamber 250.

As noted above, one aspect of the present invention includes the discovery that the passages connecting the combustion chamber with the sensor element 238 can form a resonance chamber. In the illustrated embodiment, the configuration of the sensor chamber 250, the communication passage 296, and the guide passage 292 define a resonance chamber. It has been found that the configuration of the sensor chamber 250, the communication passage 296, the guide passage 292, and the sleeve 230, affect the characteristics of the resonance chamber. In particular, the configuration of these passages and the sleeve 230 affects the frequency of resonance of the resonance chamber.

It has also been found that when the exhaust gases moving within the sensor chamber 250 and the passages 296, 292 and the sleeve 230 reach resonance, the movement of the molecules of the exhaust gases increase significantly, thus increasing a rate of heat transfer between the gases and the sleeve 230. It is believed that this increased rate of heat transfer has been at least partially responsible for overheating oxygen sensors in known oxygen sensor assemblies. For example, when the engine speed or the engine "rpm" exceeds a threshold speed, the exhaust gases within the inner housing 246 begin to resonate and increase a temperature of the sleeve, 230, the housing 228 and the sensor element 238. Thus, in the illustrated embodiment, the resonance chamber defined by the sensor chamber 250, communication passage 296, guide passage 292, and the sleeve 230 are configured such that the resonance frequency is not less than a maximum rated engine speed of the engine 46.

For example, the ECU 96 can limit the maximum rotational speed of the crankshaft 56 by cutting off fuel, causing misfiring of the sparkplugs 98, or any other known method for limiting the speed of the crankshaft 56. Typically, a maximum speed rating for an engine is based on the design of the engine. Thus, the maximum rated speed of the engine can be used as a threshold for determining the minimum resonance frequency of the resonance chamber defined in the combustion condition sensor assembly 290. Preferably, resonance chamber is tuned such that the resonance frequency occurs approximately at the maximum rate of speed dictated by the ECU 96. More preferably, the resonance chamber is tuned such that the resonance frequency is higher than the maximum rated speed of the engine 46.

FIG. 5 illustrates a modification of the assembly 290 illustrated in FIG. 4. As shown in FIG. 5, a combustion condition sensor assembly 298 is constructed substantially identical to the assembly 290 illustrated in FIG. 4, except as noted below.

As shown in FIG. 5, the sleeve 230 includes an extension 300 extending distally from the inner flange 282. As noted above, it has been discovered that by extending the sleeve 230 into the guide passage 294, the resonance frequency of the assembly 298 can be changed. Thus, depending on the maximum rated speed of the engine 46, the resonance frequency of the resonance chamber defined in the assembly 298 can be modified by changing the length of the extension 300, and/or by replacing the sleeve 230 with a sleeve having an extension with a different length.

FIG. 6 illustrates a relationship between temperature (T) of a combustion condition sensor, such as an oxygen sensor, and a resonance frequency (N) of a corresponding resonance chamber defined in a combustion condition sensor assembly housing the combustion condition sensor. As shown in FIG. 6, the temperature is plotted on the vertical axis and resonance frequency is plotted along the horizontal axis. A curve 302 is plotted on the graph of FIG. 6 and corresponds to an operating temperature of an oxygen sensor in the resonance chamebr, the resonance frequency of which has been varied. As shown in FIG. 6, the temperature of the oxygen sensor during operation of an engine remains above temperature $T_1$ over the resonance frequency range between $N_1$ and $N_2$. However, where the resonance chamber has been configured to have a resonance frequency above the resonance frequency $N_2$, the temperature T of the oxygen sensor is maintained below temperature $T_1$. Thus, where temperature $T_1$ represents a maximum safe operating temperature for a combustion condition sensor, the resonance chamber should be configured to have a resonance frequency above the resonance frequency $N_2$.

FIGS. 7–9 illustrate several further discoveries that have been made in accordance with various aspects of the present invention. For example, FIG. 7 is a graph with the inner diameter of a sleeve ($S_{ID}$)plotted on the vertical axis and resonance frequency (N) of a corresponding resonance chamber is plotted on the horizontal axis. As shown in FIG. 7, as the size of the inner diameter of the sleeve $S_{ID}$ is increased, so is the resonance frequency of the corresponding resonance chamber.

FIG. 8 is a graph having the interior volume (V) of the sensor housing graph along the vertical axis and resonance frequency (N) along the horizontal axis. A curve 306 illustrates a relationship between the interior volume of the sensor housing and the resonance frequency of the corresponding resonance chamber. As shown in FIG. 8, as the interior volume of the sensor housing V is increased, the resonance frequency N of the resonance chamber increases. In the illustrated embodiment, the sensor housing volume corresponds to the combined volume of the sensor chamber 205, the communication passage 254,296, and the guide passage 256, 292.

FIG. 9 is a graph having a length of a sleeve $L_s$, plotted along the vertical axis and resonance frequency N plotted on the horizontal axis. A curve 308 illustrates a relationship between the length of sleeve $L_s$ and resonance frequency N of a corresponding resonance chamber. As shown in FIG. 9, the curve 308 illustrates that as the length of the sleeve $L_s$ is increased, the resonance frequency N of the resonance chamber decreases.

In accordance with the disclosure set forth herein, including the relationships disclosed in FIGS. 7–9, one of ordinary skill in the art can vary the inner diameter of the sleeve 230 illustrated in FIGS. 3–5, the interior volume of the resonance chamber defined by the guide passages 258, 292, the communication passages 254, 296, and the sensor chambers 250 in accordance with the relationship disclosed in FIG. 8 to vary the resonance frequency. Further, the length of the sleeve $L_s$ can be varied by varying the length of the extension 300 illustrated in FIG. 5, so as to vary the resonance frequency of the assembly 298, as noted above. Thus, at least one of the inner diameter of the sleeve 230, the interior volume of the resonance chamber, and/or the length of the sleeve 230 can be configured such that the resonance frequency of the resonance chamber is approximately the same as the maximum rated speed of the engine 46, or more preferably, such that the resonance frequency of the resonance chamber is greater than the maximum rated speed of the engine 46.

With reference to FIG. 10, further aspect of the invention includes the realization that the output of an oxygen sensor and a direct injected two-stroke engine can be erroneous in certain engine operating states. For example, FIG. 10 is a graph having oxygen sensor output $V_O$ graphed on the vertical axis and air/fuel ratio ($\Lambda$) graphed on the horizontal axis. A first curve 308 illustrates a relationship between oxygen sensor output $V_O$ and air/fuel ratio ($\Lambda$) in an induction passage injection engine, i.e., where fuel is injected into the induction system of the engine. A second Curve 310 illustrates a relationship between oxygen sensor output $V_O$ and $\Lambda$ in a direct injected engine. It has been discovered that because air enters the cylinders of a direct injected engine without being mixed with fuel first, more air molecules reach the sensor chambers of a combustion condition sensor assembly, e.g., the sensor chambers 250 illustrated in FIGS. 3–5, as compared with induction system injected engines. Thus, an oxygen sensor of a direct injected engine is configured to be responsive in the vicinity of a Lambda value $\Lambda_D$ whereas an oxygen sensor of an induction system injected engine is configured to be responsive in the vicinity of a Lambda value $\Lambda_I$. Thus, although the oxygen sensors are calibrated to be responsive at different perceived air/fuel ratios, both configurations are calibrated to be responsive in the vicinity of approximately the ideal air/fuel ratio, i.e., approximately 14.7:1.

However, it has been discovered that in direct injected engines, the larger flow of air which is not mixed with fuel into the cylinder bores causes erroneous output of the oxygen sensor at certain engine operation conditions. For example, FIG. 11 is a graph having throttle position ($\theta$) plotted along the vertical axis and engine speed ($\omega$) plotted on the horizontal axis. One aspect of the present invention includes the discovery that at engine speeds above approximately 3000 rpm, the flow of air into the cylinder bores of a direct injected engine is sufficiently fast to cause an erroneous output from an oxygen sensor. In particular, at such engine speeds, the flow of air into the cylinder bores of such a direct injected engine, flows into the sensor chamber of an associated oxygen sensor and causes the oxygen sensor to erroneously output a signal indicative of a lean mixture.

Thus, with reference to FIG. 2, the ECU 96 preferably is configured to control the duration and timing of fuel injection of the fuel injectors 100 irrespective of the output of the combustion condition sensor 214, when the engine speed is above about 3,000 rpm. Thus, the engine control system 160 illustrated in FIG. 2 is configured to control operation of the charge former at least partially in accordance with an output of the combustion condition sensor 214, when the engine 46 is in a first operational state, and to control the charge former, e.g., the fuel injector 100, irrespective of the output of the combustion condition sensor 214, when the engine 46 is in the second operational state.

For example, the ECU 96 can be configured to control injection timing and duration of the fuel injectors 100 in accordance with the output of the oxygen sensor 232 illustrated in FIGS. 3–5 when engine speed, as determined based on the output of engine speed sensor 162, is below approximately 3000 rpm. The ECU 96 is also configured to disregard the output of the oxygen sensor 232 and to control the injection, duration and timing of the fuel injectors 100 irrespective of the output of the oxygen sensor 232 when the engine speed of the engine 46 is above approximately 3000 rpm.

With reference to FIG. 11, it has also been discovered that certain throttle positions $\theta$ of the throttle valve 90 can cause erroneous output of the oxygen sensor 232. In particular, it has been found that at throttle positions above approximately one-half of the maximum opening of the throttle valve 90 generates a flow of air into the cylinder bores 64 and the sensor chamber 250 sufficient to generate an erroneous output of the oxygen sensor 232. Thus, in an alternative embodiment, the controller 160 can be configured to control the injection timing and duration of the fuel injectors 100 based on the output of the oxygen sensor 232 when the throttle position of the throttle valve 90 is below one-half of the maximum opening and to control injection timing and duration irrespective of the output of the oxygen sensor 232 when the throttle valve 90 is opened greater than one-half of its maximum opening.

Thus, a first operational state of the engine, in which the control system 160 is configured to control the injection timing and duration of the fuel injectors 100 can be defined as being at least one of engine speeds below approximately 3000 rpm and throttle positions less than one-half of the maximum throttle valve opening. A second engine operation state in which the feedback-control system 160 controls the injection timing and duration of the fuel injectors 100 irrespective of the output of the oxygen sensor 232 can be defined as at least one of engine speeds above approximately 3000 rpm and throttle positions above approximately one-half of the maximum throttle valve opening.

By configuring the feedback-control system 160 as such, the present invention prevents erroneous output of the oxygen sensor 232 from affecting the control calculations performed by the ECU 96 and thus preventing the ECU 96 from dictating erroneous injection timing and duration information.

Although this invention has been described in terms of certain preferred embodiments, other embodiments apparent to those of ordinary skill in the art are also within the scope of this invention. For instance, various aspects of the present invention can be employed with fuel injection systems that inject fuel into other locations of the induction path other than the combustion chamber, e.g., into the intake scavenge passage. Accordingly, the scope of the invention is intended to be defined only by the claims that follow.

What is claimed is:

1. An outboard motor comprising an internal combustion engine having an engine body defining at least one combustion chamber, a sensor housing defining a sensor chamber, a sensor body having a sensor element disposed in the sensor chamber, a first passage connecting the combustion chamber with the sensor chamber, a sleeve extending within the first passage, and a plurality of flanges supporting the sleeve within the first passage so as to define a gap between an inner surface of the first passage and an outer surface of the sleeve, wherein none of the plurality of flanges contacts both the engine body and the housing.

2. The outboard motor according to claim 1, wherein the plurality of flanges comprises at least three flanges.

3. The outboard motor according to claim 1, wherein a first flange of the plurality of flanges is disposed closest to the sensor chamber, the first flange contacting only the sensor housing.

4. The outboard motor according to claim 1, wherein the sensor element comprises a portion of a combustion condition sensor.

5. The outboard motor according to claim 4, wherein the combustion condition sensor comprises an oxygen sensor.

6. An outboard motor comprising an internal combustion engine having an engine body defining at least one combustion chamber, a sensor housing having a sensor chamber, a sensor body having a sensor element disposed in the sensor chamber, a first passage connecting the combustion chamber with the sensor chamber, a sleeve extending through the first passage, at least a first flange supporting the sleeve and arranged proximate to the combustion chamber and a second flange supporting the sleeve and arranged distally from the combustion chamber, the flanges being configured to maintain a gap between an inner surface of the first passage and an outer surface of the sleeve, and an extension of the sleeve extending from the second flange and towards the sensor chamber.

7. The outboard motor according to claim 6 additionally comprising a third flange disposed between the first and second flanges.

8. The outboard motor according to claim 6 additionally comprising a second passage defined by the housing and extending between the first passage and the sensor chamber.

9. The outboard motor according to claim 8, wherein the first and second passages extend coaxially.

10. The outboard motor according to claim 9 additionally comprising a through hole formed in the housing connecting the sensor chamber with the second passage.

11. The outboard motor according to claim 10, wherein the through hole has a diameter smaller than a diameter of the sensor chamber.

12. The outboard motor according to claim 10, wherein the through hole has a diameter that is larger than a diameter of the sensor element.

13. The outboard motor according to claim 6 additionally comprising a guide passage disposed within the housing, the first passage comprising a through hole extending from the combustion chamber, the guide passage extending from the through hole and into the housing, the guide passage defining a resonance chamber.

14. An outboard motor comprising an internal combustion engine having an engine body defining at least one combustion chamber, a sensor chamber, a sensor body having a sensor element disposed in the sensor chamber, a first passage connecting the combustion chamber with the sensor chamber, a sleeve extending through the first passage, and a plurality of flanges supporting the sleeve within the first passage so as to define a gap between an inner surface of the first passage and an outer surface of the sleeve, an inner diameter of the sleeve being greater than one-half of an outer diameter defined by the outer surface of the sleeve.

15. The outboard motor according to claim 14, wherein the plurality of flanges comprises at least three flanges.

16. The outboard motor according to claim 15 additionally comprising a sensor housing defining the sensor chamber, wherein only one of the flanges contacts the housing.

17. An outboard motor comprising an internal combustion engine having an engine body defining at least one combustion chamber, a sensor housing having a sensor chamber, a sensor body having a sensor element disposed in the sensor chamber, the sensor element having an outer diameter, a through hole extending through a wall of the combustion chamber, a guide passage connecting the through hole with the sensor housing, and a communication hole connecting the guide passage with the sensor chamber, a diameter of the communication hole being larger than the diameter of the sensor element.

18. The outboard motor according to claim 17 additionally comprising a resonance chamber defined by at least the guide passage.

19. The outboard motor according to claim 18, wherein the resonance chamber is defined by at least the guide passage, the communication hole, and the collar.

20. The outboard motor according to claim 17 additionally comprising a sleeve extending at least partially within the through hole, at least a first flange and a second flange supporting the collar so as to maintain a gap between an inner surface of the through hole and an outer surface of the sleeve, the first flange disposed closest to the combustion chamber and the second flange being disposed closest to the sensor element, and an extension of the sleeve extending from the second flange into the guide passage.

21. The outboard motor according to claim 20 additionally comprising a resonance chamber defined at least partially by the extension of the sleeve.

22. The outboard motor according to claim 21, wherein a resonance frequency of the resonance chamber is affected by a length of the extension.

23. The outboard motor according to claim 21, wherein the resonance chamber is configured such that a resonance frequency of the resonance chamber is not less than approximately a maximum rated speed of the engine.

24. An outboard motor comprising an internal combustion engine having an engine body defining at least one combustion chamber, a combustion condition sensor, a housing defining a resonance chamber and being configured to receive the sensor such that the sensor is exposed to the resonance chamber, the resonance chamber being configured such that a resonance frequency of the resonance chamber is not less than approximately a maximum rated speed of the engine.

25. The outboard motor according to claim 24, additionally comprising a passage connecting the combustion chamber with the sensor and a sleeve extending within at least a portion of the passage.

26. The outboard motor according to claim 24, wherein the combustion condition sensor comprises an oxygen sensor.

27. The outboard motor according to claim 24, wherein the passage comprises a through hole defined in a wall of the combustion chamber, a guide formed in the housing and a sensor chamber defined in the housing, the sensor being received within the sensor chamber.

28. An outboard motor comprising an internal combustion engine having an engine body defining at least one combustion chamber, a combustion condition sensor, a housing defining a resonance chamber and being configured to receive the sensor such that the sensor is exposed to the resonance chamber, and means for effecting a resonance frequency of the resonance chamber to be at least as high as a maximum rated engine speed of the engine.

29. The outboard motor according to claim 28 additionally comprising a fuel charge former configured to deliver fuel charges for combustion in the combustion chamber and means for controlling the fuel charge former as a function of an output signal of the combustion condition sensor when the engine is in a first operational state and controlling the fuel charge former irrespective of an output of the combustion condition sensor when the engine is in a second operational state.

30. An outboard motor comprising an internal combustion engine having an engine body defining at least one combustion chamber, a charge former configured to deliver fuel charges to the engine body for combustion in the combustion chamber, a combustion condition sensor communicating with the combustion chamber and a controller configured to control operation of the charge former in response to an output of the combustion condition sensor when the engine is in a first operation state and to control the operation of the charge former irrespective of the output of the combustion condition sensor when the engine is in a second operation state.

31. The engine according to claim 30, wherein the engine operation state is defined by at least a first and a second engine operation characteristic.

32. The engine according to claim 31, wherein the first engine operation characteristic is engine speed.

33. The engine according to claim 32, wherein the second operation state includes engine speeds over approximately 3000 revolutions per minute.

34. The engine according to claim 32 additionally comprising a throttle valve configured to affect a flow of air into the engine body, the second engine operation characteristic being a position of the throttle valve.

35. The engine according to claim 34, wherein the second engine operation state includes throttle positions larger than approximately one-half.

* * * * *